(12) United States Patent
Nuijen et al.

(10) Patent No.: US 8,648,108 B2
(45) Date of Patent: Feb. 11, 2014

(54) MEDICAL COMPOSITIONS FOR INTRAVESICAL TREATMENT OF BLADDER CANCER

(75) Inventors: Bastiaan Nuijen, Amsterdam (NL); Ernie Pfadenhauer, Irvine, CA (US); Jos H. Beijen, Amsterdam (NL)

(73) Assignee: Spectrum Pharmaceuticals, Inc., Irvine, CA (US)

( * ) Notice: Subject to any disclaimer, the term of this patent is extended or adjusted under 35 U.S.C. 154(b) by 0 days.

(21) Appl. No.: 13/493,911

(22) Filed: Jun. 11, 2012

(65) Prior Publication Data

US 2012/0252861 A1    Oct. 4, 2012

Related U.S. Application Data

(60) Continuation of application No. 12/327,781, filed on Dec. 3, 2008, now abandoned, which is a continuation of application No. 11/531,535, filed on Sep. 13, 2006, now abandoned, which is a continuation of application No. 11/096,566, filed on Apr. 1, 2005, now abandoned, which is a division of application No. 10/285,783, filed on Nov. 1, 2002, now Pat. No. 6,894,071.

(60) Provisional application No. 60/344,446, filed on Nov. 1, 2001.

(51) Int. Cl.
*A61K 31/404* (2006.01)
*A61K 31/405* (2006.01)
*A61M 25/00* (2006.01)
*A61P 13/10* (2006.01)
*A61P 35/00* (2006.01)

(52) U.S. Cl.
USPC ............ 514/414; 514/772; 514/970; 604/48; 604/93.01

(58) Field of Classification Search
USPC ................ 514/414, 53, 58, 772, 970; 604/48, 604/93.01
See application file for complete search history.

(56) References Cited

U.S. PATENT DOCUMENTS

| | | |
|---|---|---|
| 3,993,754 A | 11/1976 | Rahman et al. |
| 4,671,954 A | 6/1987 | Goldberg et al. |
| 4,871,542 A | 10/1989 | Vilhardt |
| 4,898,729 A | 2/1990 | Miller et al. |
| 5,079,257 A | 1/1992 | Speckamp et al. |
| 5,216,011 A | 6/1993 | Paborji et al. |
| 5,292,516 A | 3/1994 | Viejas et al. |
| 5,346,703 A | 9/1994 | Viejas et al. |
| 5,405,622 A | 4/1995 | Vernice et al. |
| 5,550,110 A | 8/1996 | Cody et al. |
| 5,612,359 A | 3/1997 | Murugesan |
| 5,744,166 A | 4/1998 | Illum |
| 5,749,845 A | 5/1998 | Hildebrand et al. |
| 5,811,416 A | 9/1998 | Chwalisz et al. |
| 5,814,330 A | 9/1998 | Putteman et al. |
| 5,843,156 A | 12/1998 | Slepian et al. |
| 5,942,209 A | 8/1999 | Leavitt et al. |
| 5,993,846 A | 11/1999 | Friedman et al. |
| 6,005,020 A | 12/1999 | Loomis |
| 6,039,967 A | 3/2000 | Ottoboni et al. |
| 6,087,396 A | 7/2000 | Roberts |
| 6,123,965 A | 9/2000 | Jacob et al. |
| 6,156,348 A | 12/2000 | Santos et al. |
| 6,156,744 A | 12/2000 | Ross et al. |
| 6,171,610 B1 | 1/2001 | Vacanti et al. |
| 6,207,180 B1 | 3/2001 | Ottoboni et al. |
| 6,894,071 B2 | 5/2005 | Nuijen et al. |
| 2002/0082285 A1 | 6/2002 | Lebwohl |
| 2003/0133954 A1 | 7/2003 | Nuijen et al. |
| 2004/0009918 A1 | 1/2004 | Nedergaard et al. |
| 2004/0138121 A1 | 7/2004 | Gulati |
| 2005/0215615 A1 | 9/2005 | Nuijen et al. |
| 2006/0003987 A1 | 1/2006 | Ferraris et al. |
| 2006/0257362 A1 | 11/2006 | Gulati |
| 2007/0010570 A1 | 1/2007 | Nuijen et al. |
| 2007/0059306 A1 | 3/2007 | Grosmaire et al. |
| 2007/0185188 A1 | 8/2007 | Mirejovsky et al. |
| 2009/0163570 A1 | 6/2009 | Mirejovsky et al. |

FOREIGN PATENT DOCUMENTS

| | | |
|---|---|---|
| EP | 331635 | 9/1989 |
| EP | 338679 | 10/1989 |
| EP | 393575 | 10/1990 |
| EP | 426463 | 5/1991 |
| EP | 501523 | 9/1992 |
| EP | 642797 | 3/1995 |
| EP | 655463 A1 | 5/1995 |
| EP | 815870 A2 | 6/1997 |

(Continued)

OTHER PUBLICATIONS

Duggan et al. "Protection against aspirin-induced human gastric mucosal injury by bosentan, a new endothelin-1 receptor antagonist." Aliment Pharamcol Ther 1991: 13: 631-635.

Fabricio et al. "Essential role for endothelin ETB receptors in fever induced by LPS (*E. coli*) in rats." British Journal of Pharmacology, 1998, 125, 542-548.

Fitzsimmons et al., "Reductase enzyme expression across the national Cancer Institute tumor cell line panel: Correlation with sensitivity to MMC and EO9." J. Nat. Cancer Inst., 1996, 88(5):259-269.

Fukumura et al. "Role of Nitric Oxide in Tumor Microcirculation." American Journal of Pahtology, vol. 150, No. 2, 1997.

(Continued)

*Primary Examiner* — John Pak
(74) *Attorney, Agent, or Firm* — K&L Gates LLP; Louis C. Cullman; Brent A. Johnson

(57) ABSTRACT

Anti-cancer coating compositions comprising 3-hydroxymethyl-5-aziridinyl-1-1-methyl-2-[1H-indole-4,7-dione]propenol (E09) are disclosed. More specifically, the coating compositions comprise EO9 and a formulation vehicle. The formulation vehicle improves the solubility and stability of EO9. Additionally, the coating compositions can include coating agents that provide better adhesion of the coating composition to the bladder wall during intravesical delivery of the coating composition.

5 Claims, No Drawings

(56) References Cited

FOREIGN PATENT DOCUMENTS

| EP | 950418 A2 | 10/1999 |
|---|---|---|
| EP | 1864660 A2 | 12/2007 |
| JP | 354151134 A | 11/1979 |
| JP | 360163821 A | 8/1985 |
| JP | 361189215 A | 8/1986 |
| JP | 407215843 A | 8/1995 |
| JP | 02000256182 A | 9/2000 |
| JP | 02001010951 | 1/2001 |
| WO | 87/06227 | 10/1987 |
| WO | 96/19233 A2 | 6/1996 |
| WO | 97/23456 | 7/1997 |
| WO | 97/26864 | 7/1997 |
| WO | 99/12548 | 3/1999 |
| WO | 99/65463 | 12/1999 |
| WO | 00/33816 | 6/2000 |
| WO | 00/67023 A1 | 11/2000 |
| WO | 00/67024 A1 | 11/2000 |
| WO | 01/00198 A2 | 4/2001 |
| WO | 01/91736 A2 | 12/2001 |
| WO | 03/009805 A2 | 2/2003 |
| WO | 03/037314 A1 | 5/2003 |
| WO | 03/045434 A2 | 6/2003 |
| WO | 03/092731 A1 | 11/2003 |
| WO | 2007/092963 | 8/2007 |
| WO | 2007092964 | 8/2007 |

OTHER PUBLICATIONS

Gulati "Preface." Advanced Drug Delivery Reviews 40 (2000) 129-130.

Gulati et al. "Role of ET and NO in resuscitative effect of diaspirin cross-linked hemoglobin after hemorrhage in rat." The American Physiological Society, 1997.

Gutierrez "Mechanism of bioreductive alkylation. The example of diazaquinone (AZQ)." Free Radical Bio. Med., 1989, 6:405-445.

Hendriks, H.R., et al., "E09: A novel bioreductive alkylating indoloquinone with preferential solid tumor activity and lack of bone marrow toxicity in preclinical models." Eur. J. Cancer, 1993, 29A(6):897-906.

Herr, H.W., "Intravesical therapy—a critical review." Urol. Clin. N. Am., 1987, 14(2):399-404.

Hirst et al. "The radiosensitizer nicotinamide inhibits arterial vasocontriction." The British Journal of Radiology, 67, 795-799, 1994.

Hodnick, W.F., et al., "Measurement of dicumarol sensitive NADPH: (menadione cytochrome c) oxidoreductase activity results in an artificial assay of DT-diaphorase in cell sonicates." Anal. Biochem., 1997, 252:165-168.

Kikuchi et al. "Decreased ETB Receptor Expression in Human Metastatic Melanoma Cells." Biochemical and Biophysical Communications: 219, 734-739, 1996.

Kim et al. "The importance of DT-diaphorase and hypoxia in the cytotoxicity of RH1 in human breast and non-small cell lung cancer cell lines." Anticancer Drugs 2004;15:71-7.

Kroodsma et al. "Endothelins: possibly a new pharmacological starting point in cardiovascular disease, kidney disease and oncogicial conditions." Ned Tijdschr Geneeskd. Sep. 20, 1997;141(38):1806-10.

Kuin et al., "Potentiation of anti-cancer activity at low intratumoural pH induced by the mitochondrial inhibitor m-iodobenzylguanidine (MIBG) and its analogue benzylguanidine (BG)." Br. J. Cancer, 1999, 79(5/6):793-801.

Kuin A. et al. "Potentiation of anti-cancer activity at low intratumoural pH induced by the mitochondrial inhibitor m-iodobenzylguanidine (MIBG) and its analogue benzylguanidine (BG)." Br. J. Cancer, 1999, 79(5/6):793-801.

Kurbel et al. "Endothelin-secreting tumors and the idea of the pseudoectopic hormone secretion in tumors." Madical Hypotheses, 1999, 54(4), 329-333.

Lahav et al. "An endothelin receptor B antagonist inhibits growth and induces cell death in human melanoma cells in vitro and in vivo." Proc. Natl. Acad. Sci. USA, vol. 96, pp. 11496-11500, 1999.

Laviada et al., "Phosphatidylcholine-phospholipase C mediates the induction of nerve growth factor in cultured glial cells." FEBS Letters, 1995, 364:301-304.

Lenaz et al. "IRL-1620 increases the efficacy of radiation treatment in mice bearing lymphoma cell induced tumors." Symposium of the International-Society-of-Molecular-Evolution; Guanacaste, Costa Rica, Jan. 8-12, 2001.

Levin et al. "Immunologic Analysis of a Spinal Cord-Biopsy Specimen from a Patient with Human T-Cell Lymphotropic Virus Type I-Associated Neurologic Disease." New England Journal of Medicine 336(12):839-845, 1997.

Li et al. "Distribution of DT-diaphorase and reduced nicotinamide adenine dinucleotide phosphate: cytochrome P450 oxidoreductase in bladder tissues and tumors." The Journal of Urology, vol. 166, 2500-2505, 2001.

Mossoba, M.M., et al., "Mechanism for the reductive activation of diazaquinone." J. Pharm. Sci., 1985, 74 (12):1249-1254.

Newling, D., "Intravesical therapy in the management of superficial transitional cell carcinoma of the bladder: the experience of the EORTC GU group." Br. J. Cancer, 1990, 61:497-499.

Nicolaus, "Symbiotic Approach to Drug Design, Decision Making in Drug Research", 1983, pp. 173-186.

Nieder et al. "The role of pentoxifylline as a modifier of radiation therapy." Cancer Treatment Reviews 2005, 31, 448-455.

Nucci et al. "Pressor effects of circulating endothelin are limited by its removal in the pulmonary circulation and by the release of prostacyclin and endothelium-derived relaxing factor." Proc. Natl. Acad. Sci. USA, vol. 85, pp. 9797-9800, Dec. 1988.

Okada et al. "BQ-788, A Selective Endothelin ETB Receptor Antagonist." Cardiovascular Drug Reviews, vol. 20, No. 1, pp. 53-66, 2002.

Wu "Recent discovery and development of endothelin receptor antagonists." Expert Opinion on Therapeutic Patents, 2000, Ashley Publications Ltd.

Wulfing et al. "Endothelin-1, Endothelin-A- and Endothelin-B-receptor expression in preinvasive and invasive breast disease." Oncology Reports 11, 791-796, 2004.

Yamashita et al. "A Large Amount of Endothelin-1 is Present in Human Breast Cancer Tissues." Research Communications in Chemical Pathology and Pharmacology, vol. 74, No. 3, Dec. 1991.

Yamashita et al. "Abundant Expression of Immunoreactive Endothelin 1 in Mammary Phyllodes Tumor: Possible Paracrine Role of Endothelin 1 in the Growth of Stromal Cells in Phyllodes Tumor." Cancer Research 52, 4046-4049, 1992.

Yanagisawa et al. "A novel potent vasoconstrictor peptide produced by vascular endothelial cells." Nature vol. 332, 1988.

Yen, W.C., et al., "Different pH dependency of mitomycin C activity in monolayer and three dimensional cultures." Pharmaceut. Res., 1996, 13(12):1887-1891.

"Clinical Trials & Noteworthy treatments for Brain Tumors", http://virtualtrials.com/news3.cfm, 2 pages retrieved on Jul. 31, 2006.

Airley et al., "GLUT-1 and CAIX as intrinsic markers of hypoxia in carcinoma of the cervix; relationship to pimonidazole binding", Int J Cancer 2003; 104 : 85-91.

Alanen et al. "Augmented expression of endothelin-1, endothelini-3 and the endothelin-B receptor in breast carcinoma." Histopahtology 2000, 36, 161-167.

Arellano et al., "Influence of propylene glycol and isoropyl myristate on the in vitro percutaneous penetration of diclofenac sodium from carobpol gels", European Journal of Pharmaceutical Sciences, 7 (1998) 129-135.

Bagnato et al "Endothelin Receptor Blockade Inhibits Proliferation of Kaposi's Sarcoma Cells." American Journal of Pathology, vol. 158, No. 3, Mar. 2001.

Bagnato et al., Expression of Endothein and Endotheooine A receptor in Ovaria Carnico; evidence from an Eutocrine Torle in Tumor Growth. Cancer Research 59, 702-727, Feb. 1, 1999.

Bailey et al., "Involvement of NADPH : cytochrome p540 reductase in the activation of indoloquinone E09 to free radical and DNA damaging species". Biochemical Pharmacology, 62, 2001, 461-468.

(56) References Cited

OTHER PUBLICATIONS

Bailey, S.M., et al., Reduction of the Indoloquinone Anticancer Drug EO9 by Purified DT-Diaphorase : A detailed Kinetic Study and Analysis of Metabolites, Biochem. Pharmacol., 1998, 613-621, 56.
Basu et al. "Immunohistochemical analysis of NAD(P)H:quinone oxidoreductase and NADPH cytochrome P450 reductase in human superficial bladder tumors: relationship between tumor enzymology and clinical outcome following intravesical mitomycin C therapy." Int J Cancer 2004;109:703-9.
Bradford "A rapid and sensitive method for the quantification of microgram quantities of protein utilizing the principle of protein-dye binding." Anal. Biochem., 1976, 72:248-254.
Brooks et al. "SB 234551, a Novel Endothelin-A Receptor Antagonist, Unmasks Endothelin-Induced Renal Vasodilation in the Dog." Journal of Cardiovascular Pharmacology, 31(Suppl. 1) S339-S341, 1998.
Brown J.Martin, et al., "Hypoxia-Specific Cytotoxins in Cancer Therapy", Seminars in Radiation Oncology, vol. 6, No. 1 pp. 22-36, Jan. 1996.
Bubendorf et al. "Tissue microarray (TMA) technology: miniaturized pathology archives for high-throughput in situ studies." Journal of Pathology 2001;195: 72-9.
Butler, J., et al., "The autooxidation of reduced forms of E09." Free. Rad. Res., 1996, 25(2):141-148.
Carmeliet et al. "Angiogenesis in cancer and other diseases." Nature, vol. 407, Sep. 14, 2000.
Cecil Textbook of Medicine, 20th Edition vol. 1 W.B. Saunders Company, 1997, pp. 1004-1010.
Cemazar et al. "The endothelin B (ETB) receptor agonist IRL 1620 is highly vasoconstrictive in tow syngeneic rat tumour lines: potential for selective tumour blood flow modification." British Journal of Cancer, 2005, 93, 98-106.
Chang et al. "Expression of the human erythrocyte glucose transporter in transitional cell carcinoma of the bladder." Urology 2000;55:448-52.
Chaplin et al. "Modification of Tumour Blood Flow: Current Status and Future Directions." Seminars in Radiation Oncology, vol. 8, No. 3, 1998, pp. 151-163.
Chemical Abstracts 120: 62141, 1994.
Chemical Abstracts 122:17023 (1995).
Choudry et al., "A novel strategy for NQ01 (NAD(p)H : quinone oxidoreductase, EC 1.6.99.2) mediated therapy of bladder cancer based on the pharmacological properties of E09", British Journal of Cancer (2001) 85(8), 1137-1146.
Cliff, A.M. et al., "The effect of fasting or desmopressin before treatment on the concentration of mitomycin C during intravesical administration", BJU International, vol. 86, pp. 644-677 (2000).
Connors, T.A., "Bioreductive agents, hypoxic cells and therapy." Eur. J. Cancer, 1996, 32A(11):1833-1834.
Cummings et al., "Pharmacological and biochemical determinants of the antitumor activity of the indoloquinone E09", Biochemical Pharmacology, 1998, pp. 253-260, vol. 55, No. 3.
Cummings, J., et al., "Enzymology of MMC metabolic activation in tumor tissue. Implications for enzyme directed bioreductive drug development." Biochem. Pharmacol., 1998, 56:405-414.
Danson et al. "DT-diaphorase: a target for new anticancer drugs." Cancer Treat Rev 2004;30:437-49.
Davar et al. "Behavioral signs of acute pain produced by application of endothelin-1 to rat sciatic nerve." NeuroReport 9, 2279-2283, 1998.
Davenport et al. "Classification of endothelin receptors and antagonists in clinical development." Clinical Sciences, 2002, 103 (Suppl. 48) 15-35.
De Ascentiis, A., et al., "Mucoadhesion of poly(2-hydroxyethyl methacrylate) is improved when linear poly(ethylene oxide) chains are added to the polymer network." 1995, Journal of Controlled Release, vol. 33, pp. 197-201.
DeVries J.D. et al., A systematic study on the chemical stability of the novel indoloquinone antitumor agent EO9; abstract, International Journal of Pharmaceutics, 100 (1993) 181-188.
De Vries, J.D., et al., Pharmaceutical development of a parenteral lyophilized formulation of the novel indoloquinone antitumor agent EO9; abstract, Cancer Chemotherapy and Pharmacology, 1994, vol. 34.
Dehn et al. "Development of a new isogenic cell-xenograft system for evaluation of NAD(P)H: quinone oxidoreductase-directed antitumor quinones: evaluation of the activity of RH1." Clinical Cancer Res 2004;10:3147-55.
Del Bufalo et al. "Endothelin-1 acts as a survival factor in ovarian carcinoma cells." Clinical Science, 2002, 103 (Suppl. 48), 3025-3055.
Dirix et al., "E09 phase II study in advanced breast, gastric, pancreatic and colorectal carcinoma by the early clinical studies group." Eur. J. Cancer, 1996, 32A(11):2019-2022.
Dirix, L.Y., et al., "E09 phase II study in advanced breast, gastric, pancreatic and colorectal carcinoma by the early clinical studies group." Eur. J. Cancer, 1996, 32A(11):2019-2022.
Dong Li et al., "Distribution of DT-diaphorase and cytochrome P450 reductase in human bladder tissues and tumors", Proceedings of the American Association for Cancer Research Annual, 2001, p. 648, vol. 42.
Douglas et al. "Pharmacological evidence for the presence of three distinct functional endothelin receptor subtypes in the rabbit lateral saphenous vein." British Journal of Pharmacology, 1995, 114, 1529-1540.
Dragan J Golijanin et al., Chemoprevention of Bladder Cancer, Journal, Oct. 18, 2006, pp. 445-472, World Journal of Urology, vol. 24, No. 5.
Oosterhuis et al. "MIB-1 as a proliferative marker in transitional cell carcinoma of the bladder: clinical significance and comparison with other prognostic factors." Cancer 2000;88:2598-605.
Oosterlinck et al. Guidelines on Bladder Cancer. European Urology, 41, 105-112, 2002.
Oosterlink, et al., "A prospective European Organization for Research and Treatment of Cancer Genitourinary Group randomized trial comparing transurethral resection followed by a single instillation of epirubicin or water in single stage Ta, T1 papillary carcinoma of the bladder." J. Urol., 1993, 149:749-752.
Palit et al. "Immunodetection of GLUT-1 and NQO1 (NAD(P)H: Quinone oxidoreductase) in superficial bladder cancer." British Journal of Cancer, 2003, vol. 88, Supplement 1, p. S30, item P24.
Pan et al., "Enzymatic and pH modulation of MMC induced DNA damage in MMC resistant HCT 116 human colon cancer cells." Mol. Pharmacol., 1993, 43:870-877.
Parfitt "Analgesics Anti-inflammatory Drugs and Antipyretics." Martindale, The Complete Drug Reference 32 Edition (Edited by: Parfitt K). London, Pharmaceutical Press 1999 , 61-62.
Patel et al. "Stimulation or endothelin-1 secretion by human breast cancer cells through protein kinase A activation: a possible novel paracrine loop involving breast fibroblast-derived prostglandin E21." Molecular and Cellular Endocrinology 126, 1997, 143-151.
Phillips, R.M., "Bioreductive activation of a series of analogues of 5-aziridinyl-3hydroxymethyl-l-methyl-2-[1H-indolo-4,7-dione] prop-(3-en-a-ol (E09) by human NQO1." Biochem. Pharmacol., 1996, 52:1711-1718.
Phillips, R.M., "Inhibition of DT-diaphorase (NAD(P)H:quinine oxidoreductase, EC 1.6.99.2) by 5,6-dimethylxanthenone-4-acetic acid (DNIXAA) and flavone-8acetic acid (FAA): Implications for bioreductive drug development." Biochem. Pharmacol., 1999, 58:303-310.
Phillips, R.M., et al., "Evaluation of a novel in vitro assay for assessing drug penetration into avascular regions of tumors." Br. J. Cancer, 1998, 77(12):2112-2119.
Phillips, R.M., et al., "In vitro activity of the novel indoloquinone Eo-9 and the influence of pH on cytotoxicity." Br. J. Cancer, 1992, 65:359-364.
Plumb et al. "DT-diaphorase protects cells from the hypoxic cytotoxicity of indoloquinone EO9." Br J Cancer 1994;70:1136-43.
Plumb, J.A., et al., "Unusually marked hypoxic sensitization to indoloquinone E09 and MMC in a human colon tumor sell line that lacks NQO1 activity." Int. J. Cancer, 1994, 56:134-139.

(56) References Cited

OTHER PUBLICATIONS

Puri et al. "Phase I clinical evaluation of intravesical EOquin (EO9) against superficial bladder cancer: Preliminary results." Clinical Cancer Res 2003;9:6248S-9S.

Puri et al. "Phase I/II Pilot Study of Intravesical Apaziquone (EO9) for Superficial Bladder Cancer." The Journal of Urology, vol. 176, 1344-1348, Oct. 2006.

Rai et al. "Evidence for the involvement of ETB receptors in ET-1-induced changes in blood flow to the rat breast tumor." Cancer Chemother Pharmacol, 2003, 51:21-28.

Rajeshkumar et al. "Endothelin B receptor agonist, IRL 1620, enhances the anti-tumor efficacy of paclitaxel in breast tumor rats." Breast Cancer Research and Treatment, 2005, 94: 237-247.

Robertson et al. "Factors affecting sensitivity to E09 in rodent and human tumour cells in vitro: DT-diaphorase activity and hypoxia", European Journal of Cancer, 1994, pp. 1013-1019, vol. 30A, No. 7.

Rosenberg. Immunotherapy and gene therapy of cancer. Cancer Research, 51, 5074s-5079s, 1991.

Ross et al. "Enzymology of bioreductive drug activation." Br J Cancer 1996; Suppl 27:S1-8.

Saeki et al. "[Ala1,3,11,15]Endothelin-1 Analogs with ETB Agonistic Activity." Biochemical and Biophysical Research Communications, vol. 179, No. 1, 1991, pp. 286-292.

Santos et al. "Expression of cell-cycle regulatory proteins and their prognostic value in superficial low-grade urothelial cell carcinoma of the bladder." Eur J Surg Oncol 2003;29:74-80.

Santos et al. "Ki-67 index enhances the prognostic accuracy of the urothelial superficial bladder carcinoma risk group classification." Int J Cancer 2003;105: 267-72.

Sartorelli et al. "Mitomycin C: a prototype bioreductive agent." Oncol Res 1994;6:501-8.

Saunders et al., "The relative importance of NADPH:cytochrome c (P450) reductase for determining the sensitivity of human tumor cells to the indoloquinone E09 and related analogues lacking functionality at the C-2 and C-3 positions." Biochem. Pharmacol., 2000, 59:993-996.

Sawhney et al., "Neo-adjuvant chemotherapy for muscle-invasive bladder cancer : a look ahead". Annals of Oncology, 17, 1360-1369, 2006.

Schellens et al., "Phase I and pharmacologic study of the novel indoloquinone bioreductive alkylating cytotoxic drug En", Journal of the National Cancer Institute, 1994, pp. 906-912, vol. 86, No. 12.

Schlager, J.J., et al., "MMC is not metabolized by but is an inhibitor of human kidney NAD(P)H:quinone acceptor) oxidoreductase." Cancer Chemother. Pharmacol., 1988, 22:126-130.

Siegel, D., et al., "Immunohistochemical detection of NAD(P)H:Quinone oxidoreductase in human lung and lung tumors." Clin. Cancer Res., 1998, 4:2065-2070.

Siegel, D., et al., "Metabolism of MMC by NQO1: role in MMC induced DNA damage and cytotoxicity in human colon carcinoma cells." Cancer Res., 1990, 50:7483-7489.

Siegel, D., et al., "PH dependent inactivation of NQO1 by MMC and porfiromycin." Mol. Pharmacol., 1993, 44:1128-1134.

Smitskamp-Wilms E., et al., "Development, Pharmacology, Role of DT-Diaphoras and Prospects for the Indologuinone EO0, General Pharmacology, vol. 27, No. 3 pp. 421-429, 1996."

Smitskamp-Wilms, E., et al., "Chemosensitivity to the indoloquinone E09 is correlated with DT-diaphorase activity and its gene expression." Biochem. Pharmacol., 1994, 47(8):1325-1332.

Smitskamp-Wilms, E., et al., "NQ01 activity in normal and neoplastic human tissues: An indicator of sensitivity to bioreductive agents?" Br. J. Cancer, 1995, 72:917-921.

Sonveaux et al. "Endothelini-1 is a critical mediator of myogenic tone in tumor arterioles: implications for cancer treatment." Cancer Research 64, 3209-3214, 2004.

Spanswick, V.J., et al., Pharmacological Determinants of the Antitumour Acitivity of Mitomycin C, Biochem. Pharmacol., 1998, 1497-1503, 56.

Sylvester et al. "A single immediate postoperative instillation of chemotherapy decreases the risk of recurrence in patients with stage Ta T1 bladder cancer: a metaanalysis of published results of randomized clinical trials." J. Urol. 2004, 171 (6 Pt 1):2186-90.

Tolley, D.A., et al., "The effect of intravesical MMC on recurrence of newly diagnosed superficial bladder cancer: A further report with 7 tears of followup." J. Urol. 1996, 155:1233-1238.

Traver, R.D., et al., "NAD(P)H:guinine oxidoreductase gene expression in human colon carcinoma cells: Characterisation of a mutation which modulates NQ01 activity and mitomycin sensitivity." Cancer Res., 1992, 52:797-802.

Vainchtein et al. "Quantitative analysis of EO9 (apaziquone): and its metabolite EO5a in human plasma by high-performance liquid chromatography under basic conditions coupled to electrospray tandem mass spectrometry", Journal of Mass Spectrometry. 2006, pp. 1268-1276, vol. 41.

Vainchtein et al., "Stability experiments in human urine with EO9 (apaziquone): A novel anticancer agent for the intravesical treatment of bladder cancer", Journal of Pharmaceutical and Biomedical Analysis, 2006, pp. 285-292, vol. 43.

Van Der Heijden et al. "Phase II Marker Lesion Study with Intravesical Instillation of Apaziquone for Superficial Bladder Cancer: Toxicity and Marker Response." The Journal of Urology, vol. 176, 1349-1353, Oct. 2006.

Van Der Schoot et al. "EO-9 bladder instillations: Formulation selection based on stability characteristics and in vivo stimulation studies." International Journal of Pharmaceutics 329, 2007, 135-141.

Van Der Schoot et al., "Development of a bladder instillation of the indoloquinone anticancer agent EO9 using tert-butyl alcohol as lyophilizatio vehicle", Chapter 1.1, Pharmaceutical development of investigational anticancer agents: focus on EO9, AP5346, and GMP implications, 2006, pp. 19-44.

Walton, M.I., et al., "The role of NAD(P)H:quinine reductase (EC 1.6.99.2, NQO1) in the reductive bioactivation of the novel indoloquinone antitumour agent E09." Cancer Commun., 1991, 3(7):199-206.

Warde et al., World J. Urol. 15 : 125-133 (1997).

Wardman et al. "Radicals from one-electron reduction of nitro compounds, aromatic N-oxides and quinones: the kinetic basis for hypoxia-selective, bioreductive drugs." Biochem Soc Symp 1995;61:171-94.

Workman et al. "The experimental development of bioreductive drugs and their role in cancer therapy." Cancer Met Rev 1993;12:73-82.

Workman, P., "Enzyme directed bioreductive drug development revisited: A commentary on recent progress and future prospects with emphasis on quinine anticancer drugs and quinine metabolizing enzymes, particularly NQO1." Oncol. Res., 1994, (Oct. 2011) 6:461-475.

Chaplin, David J., Ph.D. Session E: Bioreductive Therapies: Keynote Address: Bioreductive Therapy. Int. J. Radiation Oncology Biol. Phys., vol. 22, pp. 685-687 (1992).

Battistini et al. "Endothelins: A Quantum Leap Forward." DN&P 8(6), Aug. 1995.

Belcourt et al. "Differential toxicity of mitomycin C and porfiromycin to aerobic and hypoxic Chinese hamster ovary cells overexpressing human NADPH:cytochrome c (P-450) reductase." Proc Natl Acad Sci USA 1996;93:456-60.

Bell et al. "A Comparative Study of Tumour Blood Flow Modification in Two Rat Tumour Systems Using Endotelin-1 and Angiotensin II: Influence of Tumour Size on Angiotensin II Response." Int. J. Cancer: 67, 730-738, 1996.

Bell et al. "Effect of Endothelin-1 and Sarafotoxin S6c on Blood Flow in a Rat Tumor." Journal of Cardiovascular Pharmacology, 26(Suppl. 3) S222-S225, 1995.

Bell et al. "Modification of Blood Flow in the HSN Tumour and Normal Tissues of the Rat by the Endothelin ETB Receptor Agonist, IRL 1620." Int. J. Cancer: 80, 295-302, 1999.

Bell et al. "Tumour blood flow modification by endothelin-related peptides in the rat HSN fibrosarcoma." British Journal of Cancer (1996) 74, S161-S163.

Bell et al. "Vascular Response of Tumour and Normal Tissues to Endothelin-1 Following Antagonism of ETA and ETB Receptors in Anesthetized Rats." Int. J. Cancer: 73, 283-289, 1997.

(56) References Cited

OTHER PUBLICATIONS

Bhalla et al. "Potentiation of morphine analgesia by BQ123, an endothelin antagonist." Peptides 23, 2002, 1837-1845.

Bhargava et al. "Modification of Brain and Spinal Cord Dopamine D1 Receptors Labeled with [3H]SCH 23390 After Morphine Withdrawal from Tolerant and Physically Dependent Rats1." The Journal of Pharmacology and Experimental Therapeutics, vol. 252, No. 3, 1990.

Bladder Cancer article, Cancer Research UK.

Blanchet et al. "Prospective evaluation of Ki-67 labeling in predicting the recurrence and progression of superficial bladder transitional cell carcinoma." Eur Urology 2001;40:169-75.

Hoskin et al. "GLUT1 and CAIX as intrinsic markers of hypoxia in bladder cancer: relationship with vascularity and proliferation as predictors of outcome of ARCON." British Journal of Cancer 2003;89:1290-1297.

Hussain et al. "Long-term results of a phase II study of synchronous chemoradiotherapy in advanced muscle invasive bladder cancer." British Journal of Cancer 2004;90:2106-2111.

Inoue et al. "The human endothelin family: Three structurally and pharmacologically distinct isopeptides predicted by three separate genes." Proc. Natl. Acad. Sci., vol. 86, pp. 2863-2867, 1989.

Jarvis et al. "ABT-627, an endothelin ETA receptor-selective antagonist, attenuates tactile aooldynia in a diabetic rat model of neuropathic pain." European Journal of Pharmacology 388, 2000, 29-35.

Jonkman-De Vries et al., "Pharmaceutical development of a parenteral lyophillized formulation of the novel indoloquinone antitumor agent EO9", Cancer Chemother Pharmacol; 1994; 34(5) : 416-22.

Jordan et al. "Changes in tumor oxygenation/perfusion induced by the no donor, isosorbide dinitrate, in comparison with carbogen: monitoring by EPR and MRI." Int. J. Radiation Oncology Biol. Phys., vol. 48, No. 2, pp. 565-570, 2000.

Jordan et al. "Insulin Increases the Sensitivity of Tumors to Irradiation: Involvement of an Increase in Tumor Oxygenation Mediated by a Nitric Oxide-dependent Decrease of the Tumor Cells Oxygen Consumption." Cancer Research 62, 2555-3561, 2002.

Jordan et al. "Potentiation of Radiation-Induced Regrowth Delay by Isosorbide Dinitrate in FSAII Murine Tumors." Int. J. Cancer: 103, 138-141, 2003.

Kantoff et al., "Bladder Cancer, Neoplasms of the Genitourinary Tract", Chapter 107, pp. 1543-1558.

Kennedy et al., "Proliferation and hypoxia in human squamous cell carcinoma of the cervix: First report of combined immunohistochemical assays." Int. J. Radiat. Oncol. Biol. Phys., 1997, 37(4):897-905.

Kennedy, A.S., et al., "Proliferation and hypoxia in human squamous cell carcinoma of the cervix: First report of combined immunohistochemical assays." Int. J. Radiat. Oncol. Biol. Phys., 1997, 37(4):897-905.

Li et al., "Distribution of DT-diaphorase and cytochrome P450 reductase in human bladder tissues and tumors." Proceedings of the American Association for Cancer Research Annual Meeting, Mar. 2001, 42:648.

Loadman, P.M., et al., "Pharmacological Approach Towards the Development of Indolequinone Bioreductive Drugs Based on the Clinically Inactive Agent E09", Br. J. Pharmacol., 2002, 701-709, 137.

Maffezzini, M., et al., "Up-front chemotherapy for low stage low grade recurrent bladder cancer." L. Urol., 1996, 155:91-93.

Maliepaard, M. et al., "Indoloquinone E09: DNA interstrand cross linking upon reduction by DT-diaphorase or xanthine oxidase." Br. J. Cancer, 1995, 71:836-839.

Malkinson, A.M., et al., "Elevated NQO1 activity and messenger RNA content in human non small cell lung carcinoma—Relationship to the response of lung tumor xenografts to MMC." Cancer Res., 1992, 52(12):4752-4757.

Martinive et al. "Reversal of temporal and spatial heterogeneities in tumor perfusion identifies the tumor vascula tone as a tunable variable to improve drug delivery." Mol Cancer Ther 2006;5(6).

Matsumaru et al. "Bosentan, a novel synthetic mixed-type endothelin receptor antagonist, attenuates acute gastric mucosal lesions induced by indomethacin and HCl in the rat: Role of endogenous endothelin-1." J Gastroenterol 1997; 32:164-170.

Medline abstract 1987238242 (1987).

Medline Abstract 2001071878 (Entered Medline Jan. 4, 2001).

Medline Abstract 92362735, 1992.

Mitomycin-C 2mg Powder for Injection/Mitomycin-C 10mg Powder for Injection. South African Electronic Package Inserts, home.intekom.com/.../mitomyc.html.

MEDICAL COMPOSITIONS FOR INTRAVESICAL TREATMENT OF BLADDER CANCER

CROSS REFERENCE TO RELATED APPLICATIONS

This application is a continuation of U.S. patent application Ser. No. 12/327,781, filed Dec. 3, 2008, which is a continuation of U.S. patent application Ser. No. 11/531,535, filed Sep. 13, 2006, which is a continuation of U.S. patent application Ser. No. 11/096,566 filed Apr. 1, 2005, which is a division of U.S. patent application Ser. No. 10/285,783 filed Nov. 1, 2002, now U.S. Pat. No. 6,894,071, which claims the benefit of U.S. Provisional Application No. 60/344,446, filed Nov. 1, 2001, the entire contents of which are hereby incorporated by reference.

BACKGROUND OF THE INVENTION

Bladder cancer accounts for approximately 2% of all malignant cancers and is the fifth and tenth most common cancer in men and women, respectively. The American Cancer Society estimated that 54,500 new cases and 11,700 deaths would have occurred in 1997. Superficial bladder cancers (pTa, pT1 and CIS) account for 70-80% of cancers at first presentation. Management of superficial bladder cancer may be achieved by endoscopic surgical resection often followed by a course of adjuvant intravesical chemotherapy or immunotherapy with the aim of both eradicating remaining tumor cells and preventing tumor recurrence (Herr H W (1987) Intravesical therapy—a critical review. *Urol Clin N Am* 14:399-404). Both anti-neoplastics (Mitomycin C [MMC], epirubicin and thioTEPA) and immunotherapy (BCG) administered intravesically are effective at reducing tumor recurrence rates although it is unclear whether disease progression to muscle invasive tumors is prevented (Newling D (1990) Intravesical therapy in the management of superficial transitional cell carcinoma of the bladder: the experience of the EORTC GU group, *Br J Cancer* 61:497-499; Oosterlink et al. (1993) A prospective European Organization for Research and Treatment of Cancer Genitourinary Group randomized trial comparing transurethral resection followed by a single instillation of epirubicin or water in single stage Ta, T1 papillary carcinoma of the bladder. *J Urol* 149:749-752). This observation in conjunction with the fact that mortality from bladder cancer is still high underscores the need to develop more effective therapeutic agents (Oosterlink et al. 1993).

One such therapeutic agent is MMC which belongs to a class of compounds known as bioreductive drugs (Workman 1994). MMC represents one of the antineoplastic agents used to treat superficial bladder cancers (Maffezzini et al, 1996, Tolley et al, 1996). MMC is activated to a cytotoxic species by cellular reductases although the role of specific reductase enzymes involved in bioreductive activation remains poorly defined and controversial (Cummings et al, 1998a). This is particularly true for the enzyme NQO1 (NAD(P)H:Quinone oxidoreductase, EC 1.6.99.2) which is a cytosolic flavoprotein which catalyses the two electron reduction of various quinone based compounds using either NADH or NADPH as electron donors (Schlager and Powis, 1988, Siegel et al, 1990). The structurally related compound E09 (5-aziridinyl-3-hydroxymethyl-1methyl-2-[1H-indole-4,7-dione]prop-(3-en-a-ol), is however a much better substrate for NQO1 than MMC (Walton et al, 1991) and a good correlation exists between NQO1 activity and chemosensitivity in vitro under aerobic conditions (Robertson et al, 1994, Fitzsimmons et al, 1996, Smitkamp-Wilms et al, 1994). Under hypoxic conditions however, EO9's properties are markedly different with little or no potentiation of EO9 toxicity observed in NQO1 rich cells (Plumb and Workman, 1994). In NQO1 deficient cell lines however, large hypoxic cytotoxicity ratios have been reported (Workman, 1994). Therefore, EO9 has the potential to exploit the aerobic fraction of NQO1 rich tumors or the hypoxic fraction of NQO1 deficient tumors (Workman, 1994).

EO9 has been clinically evaluated but despite reports of three partial remissions in phase I clinical trials, no activity was seen against NSCLC, gastric, breast, pancreatic and colon cancers in subsequent phase II trials (Schellens et al, 1994, Dirix et al, 1996). These findings are particularly disappointing in view of the preclinical studies (Hendriks et al, 1993) together with reports that several tumor types have elevated NQ01 levels (Malkinson et al, 1992, Smitkamp-Wilms et al, 1995, Siegel et al, 1998). Several possible explanations have been proposed to explain EO9's lack of clinical efficacy (Connors, 1996, Phillips et al, 1998). Recent studies have demonstrated that the failure of E09 in the clinic may not be due to poor pharmacodynamic interactions but may be the result of poor drug delivery to tumors (Phillips et al, 1998). The rapid plasma elimination of E09 (tl/z=10 min in humans) in conjunction with poor penetration through multicell layers suggests that E09 will not penetrate more than a few microns from a blood vessel within its pharmacokinetic lifespan (Schellens et al, 1994, Phillips et al, 1998). Intratumoural administration of E09 to NQ01 rich and deficient tumors produced significant growth delays (although a distinction between damage to the aerobic or hypoxic fraction was not determined) suggesting that if E09 can be delivered to tumors, therapeutic effects may be achieved (Cummings et al, 1998b). While these undesirable characteristics are a serious setback for the treatment of systemic disease, paradoxically they may be advantageous for treating cancers which arise in a third compartment such as superficial bladder cancer. In this scenario, drug delivery is not problematical via the intravesical route and the penetration of E09 into avascular tissue can be increased by maintenance of therapeutically relevant drug concentrations within the bladder (using a one hour instillation period for example). While this method of instilling EO9 within the bladder may be useful, there still remains a need for drug delivery vehicles that are capable of delivering an effective amount of EO9 within the bladder.

BRIEF SUMMARY OF THE INVENTION

In a broad aspect, the present invention is directed to compositions for treating cancer. More specifically, the compositions of the present invention comprise pharmaceutical products formulated for intravesical instillation to treat bladder cancer. The pharmaceutical products comprise bioredutive alkylating indoloquinone with anti-tumor effects such as, but not limited to, 3-hydroxymethyl-5-aziridinyl-1-1-methyl-2-[1H-indole-4,7-dione]propenol (E09) and a formulation vehicle. The formulation vehicles of the present invention improves the physical characteristics of the solution such as solubility, lyophilization, and ease of reconstitution of the lyophilized solution.

According to one embodiment of the present invention, the composition of the present invention comprises 3-hydroxymethyl-5-aziridinyl-1-1-methyl-2-[1H-indole-4,7-dione]propenol (EO9) and a formulation vehicle. According to one embodiment, the formulation vehicle is a mixture of tert-butanol and water. In another embodiment, the formulation vehicle is a mixture of ethanol and water. In yet another embodiment, the formulation vehicle is 2-hydroxypropyl-β-cyclodextrin. These composition embodiments of the present invention can be lyophilized by techniques known or developed in the art. The lyophilized compositions of the present invention are According to another embodiment of the present invention, the composition of the present invention comprises EO9 and a coating agent. The coating agent allows for better adhesion of the composition to the bladder wall. Consequently, the composition and, in particular, the EO9 contacts and may be able to penetrate the avascular tissue that comprises for a time sufficient to treat the bladder cancer. In one embodiment of the present invention, the coating agent is propylene glycol. In other exemplary embodiments of the present invention, the coating agent can be selected from the group consisting of hydroxypropylcellulose, carboxymethylcellulose, chitosan hydrochloride, lectin, or polycarbophil. In yet another embodiment of the present invention, the compositions of the present invention can be delivered to the bladder wall by a liposome. In another embodiment, the compositions of the present invention can be delivered to the bladder wall by a microsphere. In another embodiment, the compositions of the present invention can be delivered to a patient intravenously.

The present invention relates to methods and compositions for treating bladder cancer. In one embodiment of the present invention an anti-cancer effective amount of 5-aziridinyl-3-hydroxymethyl-1-methyl-2-[1H-indole-4,7-dione]prop-β-en-α-ol (EO9) is administered to a patient suffering from lack cancer susceptible to EO9.

In another embodiment in anti-cancer effective amount of EO9 is administered to a patient suffering from bladder cancer susceptible to EO9 wherein the EO9 is administered directly to the bladder using, among other techniques, a catheter. In another non-limiting embodiment EO9 is aseptically injected into the bladder.

In another embodiment EO9 is compounded in a composition such that when administered directly to the bladder an anti-cancer effective amount of EO9 is maintained in contact with the bladder wall, and therefore tumor, for a time sufficient to have an anti-cancer to effect.

In another embodiment of the present invention EO9 is compounded with propylene glycol allowing better adhesion to the bladder wall. In another embodiment the present invention is compounded with at least one member of the group comprising propylene glycol, hydroxypropylcellulose, carboxymethylcellulose, chitosan hydrochloride, lectin and or polycarbophil.

In another embodiment EO9 containing compositions are provided that, when administered to a patient, are retained within the bladder in such a fashion that an anti-cancer effective amount of EO9 is maintained in contact with the bladder wall for a time sufficient to treat bladder cancer.

DETAILED DESCRIPTION OF THE INVENTION

The embodiments of the present invention are directed to compositions for treating bladder cancer via intravesical instillation. According to one embodiment, the composition of the present invention comprises 3-hydroxymethyl-5-aziridinyl-1-1-methyl-2-[1H-indole-4,7-dione]propenol (EO9) and a formulation vehicle. The formulation vehicles of the present invention are solvents that improves the solubility and stability of EO9. In a broad aspect of the present invention, the formulation vehicles of the present invention can be a mixture of an alcohol and water. According to the various embodiments of the present invention, EO9 dissolves in the formulation vehicles without physical manipulation such as grinding. Because the compositions of the present invention are capable of dissolving greater amounts of EO9, additional flexibility with respect to dosage units is achieved. According to one embodiment, a content of 8.0 mg of EO9 per dosage unit is contemplated. In other embodiments, instillation doses range from approximately 0.5 mg to approximately 16 mg in a total volume of 40 mL.

In addition to improving the solubility of EO9, the formulation vehicles of the present invention are good lyophilization vehicles. For example, the formulation vehicles of the present invention minimizes the time to lyophilize the compositions of the present invention. Accordingly, in one embodiment of the present invention, it is possible to lyophilize the compositions of the present invention in less than approximately 4.5 days. Furthermore, the compositions of the present invention are stable after undergoing lyophilization (see table 4). It is believed that the formulation vehicles of the present invention minimize the crystallization of EO9 during the lyophilization process. Consequently, by reducing the amount of crystallization of EO9, a smaller volume of fluid is required to reconstitute the compositions of the present invention. As a result, a larger batch size can be achieved due to the reduced reconstitution volumes for the lyophilized composition.

According to one embodiment, the composition of the present invention comprises EO9 and a formulation vehicle comprising tert-butanol. According to another embodiment of the present invention, the formulation vehicle comprises mixture of ethanol and water. In yet another embodiment, the formulation vehicle is 2-hydroxypropyl-β-cyclodextrin. In one exemplary embodiment, the formulation vehicle comprises 40% tert-butanol in water. As those skilled in the art will appreciate, the amount of tert-butanol may be varied. The tert-butanol solution better dissolves EO9 as compared to water. By utilizing a tert-butanol formulation vehicle, solubility of EO9 is at least 9.5 mg/ml whereas the solubility of EO9 is approximately 0.2 mg/ml in water. Consequently, a smaller volume of the tert-butanol is required to dissolve a given amount of EO9. Additionally, a greater amount of EO9 may be dissolved in a given solution. That is, the compositions of the present invention will have a higher concentration of EO9 as compared to a solution where EO9 is dissolved in water.

According to another embodiment of the present invention, the composition comprises, EO9, a formulation vehicle, and a bulking agent. In one exemplary embodiment, lactose can be utilized as the bulking agent. As those skilled in the art will appreciate, it is contemplated that other bulking agents known or developed in the art may be utilized. According to another exemplary embodiment, the composition of the present invention can be buffered. In one embodiment, the composition is buffered to a pH ranging from approximately 9 to approximately 9.5. The composition can be buffered with any known or developed buffering agents. The compositions of the present invention can either be compounded for intravesical delivery or lyophilized. As those skilled in the art will appreciate, the compositions of the present invention can be lyophilized by those methods known or developed in the art. The lyophilized compositions can be reconstituted by a reconstitution vehicle. According to one exemplary embodiment, the reconstitution vehicle comprises 2% sodium bicarbonate, 0.02% disodium edetate and propylene glycol:water (60:40 V/V). This reconstitution vehicle dissolves the lyophilized composition of the present invention and produces a stable solution for administration for up to 24 hours. Additionally, the reconstitution vehicle of the present invention provides an ampoule having an extractable volume of 5 mL of reconstituted EO9 comprising propylene glycol/water/sodium bicarbonate/sodium edetate 60/40/2/0.02% v/v/w/w.

In another aspect of the present invention, the compositions of the present invention also comprises coating agents. The coating agents of the present invention provide better adhesion of the composition to the bladder wall. Consequently, the composition and, in particular, the EO9 contacts and may be able to penetrate the avascular tissue that comprises for a time sufficient to treat the bladder cancer. In one embodiment of the present invention, the coating agent is propylene glycol. In other exemplary embodiments of the present invention, the coating agent can be selected from the group consisting of hydroxypropylcellulose, carboxymethylcellulose, chitosan hydrochloride, lectin, or polycarbophil.

In yet another embodiment of the present invention, the compositions of the present invention can be delivered to the bladder wall by a liposome. According to one embodiment of the present invention, the liposomes used are unilamellar or multilamellar and contain at least one cationic phospholipid such as stearylamine, 1,2-diacyl-3-trimethylammonium-propane (TAP) or 1,2-triacyl-3-dimethylammonium-propane (DAP). In another embodiment of the present invention, the surface liposomes may be coated with polyethylene glycol to prolong the circulating half-life of the liposomes. In yet another embodiment of the present invention, neutrally charged liposomes such as, but not limited to, phosphatidylcholine and cholesterol can also be used for liposomal entrapment of the compositions of the present invention. In another embodiment, the compositions of the present invention can be delivered to the bladder wall by a microsphere such as those known or developed in the art.

In yet another embodiment, the compositions of the present invention can be delivered to a patient intravenously. The lyophilized composition of the present invention can be reconstituted using the formulation vehicles of the present invention. The reconstituted composition can then be diluted to a desired concentration and delivered to a patient intravenously.

The following experiments were conducted to determine the activity of NQ01 in a series of human bladder tumors and normal bladder tissue by both enzymatic and immunohistochemical techniques. Furthermore, the following experiments evaluate strategies for reducing possible system toxicity arising from intravesical therapy based upon the fact that the aerobic activity of EO9 against cell lines is enhanced under mild acidic conditions (Phillips et al., 1992). Administration of EO9 in an acidic vehicle would result in greater activity within the bladder and any drug absorbed into the blood stream would become relatively inactive due to the rise in extracellular pH. The following experiments also determine the role of NQ01 in the activation of EO9 under acidic conditions.

Collection of tumor and normal bladder specimens. Ethical approval for tissue collection was obtained from the Local Research Ethical Committee (Bradford NHS Trust) and samples taken from patients following informed consent. A total of 17 paired cold pinch biopsies were taken from bladder tumors and macroscopically normal looking bladder mucosa at cystoscopy, immediately prior to formal transurethral resection of the tumor. Three specimens were taken from patients undergoing cystectomy and tumor and normal samples dissected by pathologists within one hour of surgical removal. Specimens were flash frozen in liquid nitrogen and transported for NQO1 enzyme analysis. Further biopsies were taken of the normal bladder mucosa immediately adjacent to the previous biopsy site and sent at the end of the procedure, along with the resected tumor, in formalin for routine histological analysis. In this way bladder tumor and normal bladder urothelium enzymology could be directly correlated with the appropriate tissue histology in each patient. Immunohistochemistry was performed from the subsequently archived wax blocks prepared for histology.

Biochemical determination of NQO1 activity. Cell cultures in exponential growth were trypsinised, washed twice with Hanks balanced salt solution (HBSS) and sonicated on ice (3×30 sec bursts at 40% duty cycle and output setting 4 on a Semat 250 cell sonicator). NQO1 activity and protein concentration was determined as described below. Tissues were homogenised (10% w/v homogenate) in sucrose (0.25M) using a 1ml tissue homogeniser (Fisher Scientific). Cytosolic fractions were prepared by centrifugation of the homogenate at 18,000 g for 4 min followed by further centrifugation of the supernatant at 110,000 g for 1 h at 4° C. in a Beckman Optima TL ultracentrifuge. Activity of NQO1 in the supernatant was determined spectrophotometrically (Beckman DU650 spectrophotometer) by measuring the dicumarol sensitive reduction of dichlorophenolindophenol (DCPIP, Sigma Aldrich, UK) at 600 nm (Traver et al, 1992). This assay has been extensively validated for use in measuring NQO1 activity in both tissue and cell homogenates and has been shown to be preferable to other assays for NQO1 activity (Hodnick and Sartorelli, 1997). Each reaction contained NADH (200 lzM), DCPIP (40/iM, Sigma Aldrich, UK), Dicumarol (20 uM, when required, Sigma Aldrich, UK), cytosolic fraction of tissues (50 p,l per assay) in a final volume of 1 ml Tris HCl buffer (50 mM, pH 7.4) containing bovine serum albumin (0.7 mg ml$^{-1}$, Sigma Aldrich, UK). Rates of DCPIP reduction were calculated from the initial linear part of the reaction curve (30 s) and results were expressed in terms of nmol DCPIP reduced/min/mg protein using a molar extinction coefficient of 21 mNT' cm$^{-1}$ for DCPIP. Protein concentration was determined using the Bradford assay (Bradford, 1976).

Immunohistochemistry. Polyclonal antibodies (raised in rabbits) to purified rat NQO1 were a gift from Professor Richard Knox (Enact Pharma Plc). Validation of the antibody for use in immunohistochemistry studies was performed by Western blot analysis using both purified human recombinant NQO1 and cell extracts derived from a panel of cell lines of human origin. These cell lines included H460 (human NSCLC), RT112 (human bladder carcinoma), HT-29 (human colon carcinoma), BE (human colon carcinoma), MT1 (human breast) and DLD-1 (human colon carcinoma). The BE cell line has been genotyped for the C609T polymorphic variant of NQOI and is a homozygous mutant (and therefore devoid of NQO1 enzyme activity) with respect to this polymorphism (Traver et al, 1992). Cells were washed in ice cold phosphate buffered saline and lysed by sonication (30 seconds on ice) in Tris HCl (50 mM, pH 7.5) containing 2 mM EGTA, 2 mM PMSF and 25 Ftg ml$^{-1}$ leupeptin. Protein concentration was estimated using the Bradford assay (Bradford, 1976) and a total of 12.5, ug of protein (in Lamelli sample loading buffer) applied to a 12% SDS-PAGE gel. Following electrophoretic transfer to nitrocellulose paper, membranes were blocked in TBS/Tween 20 (0.1%) containing 5% non-fat dry milk for 1 h at room temperature. Membranes were washed in TBS/Tween 20 (0.1%) prior to the addition of rabbit anti-rat NQO1 antibody (1:100 dilution) and incubated at room temperature for I h. Membranes were extensively washed in TBS/Tween 20 (0.1%) followed by the addition of anti-rabbit IgG horseraddish peroxidase conjugated secondary antibody (1:5000 dilution in TBS/Tween 20). Proteins were visualised by ECL based chemiluminescence as described by the manufacturer (Amersham Pharmacia Biotech, Bucks, UK).

For immunohistochemical studies, all tissues (both tumor and normal bladder mucosa) were fixed in 10% formalin, processed routinely and embedded in paraffin wax. Two sections of each tissue block were placed on one slide, one section served as the test and the other as a negative control (no primary antibody). A total of 5 sections from each sample were stained for NQO1 (plus negative controls) and tumor and normal samples from a total of 17 patients were analysed. Sections (5, um) were dewaxed, rehydrated and incubated with primary antibody (1:400 dilution) for 4 hours. Sections were then washed and incubated with biotinylated mouse anti rabbit IgG for 30 min prior to immunoperoxidase staining using VECTASTAIN ABC reagents and DAB (Vector Laboratories Ltd, Peterborough, UK). Sections were counterstained with haematoxylin according to standard procedures.

Cell culture and chemosensitivity studies. E09 was a gift from NDDO Oncology, Amsterdam and MMC was obtained from the Department of Pharmacy, St Lukes Hospital, Bradford. H460 (human NSCLC) cell line was obtained from the American Type Culture Collection (ATCC). HT-29 (human colon carcinoma), RT112/83 (human bladder carcinoma epithelial), EJ138 (human bladder carcinoma) and T24/83 (human bladder transitional cell carcinoma) cell lines were obtained from the European Collection of Animal Cell Cultures (ECACC). A2780 (human ovarian carcinoma) and BE (human colon carcinoma) cells were gifts from Dr T Ward (Paterson Institute, Manchester, UK). All cell lines were maintained as monolayer cultures in RPNII 1640 culture medium supplemented with fetal calf serum (10%), sodium pyruvate (2 mM), L-glutamine (2 mM), penicillin/streptomycin (50 IU/ml/50 jug/ml) and buffered with HEPES (25 mK. All cell culture materials were purchased from Gibco BRL (Paisley, UK). Cells were exposed to MMC or E09 at a range of doses for one hour and chemosensitivity was assessed following a five day recovery period using the MTT assay, details of which have been described elsewhere (Phillips et al, 1992). The pH of the medium used during drug exposure was adjusted using small aliquots of concentrated HCl (40, A conc HCl [10.5M] to 20 ml medium gives a pH of 6.0). Calibration curves were conducted over a broad range of pH values in culture medium (pH 3.5 to 11) and the stability of the pH conditions monitored over a one hour incubation period at 37° C. At all pH values, no significant changes in the pH of the medium was observed over the one hour drug exposure period (data not presented).

HT-29 multicell spheroids were prepared by seeding $5\times10^5$ cells into T25 flasks which had been based coated with agar (1% w/v) and incubated for 24 h at 37° C. Immature spheroids were then transferred to a spinner flask (Techne) containing 250 ml of RPMI 1640 growth medium and spheroids were kept in suspension by stirring at 50 rpm. When spheroids reached a diameter of approximately 500 Am, they were harvested for chemosensitivity studies. Multicell spheroids were exposed to a range of E09 concentrations at pHe 6.0 and 7.4 for one hour at 37° C. Following drug incubation, spheroids were washed twice in HBSS prior to dissagregation into single cells using trypsin EDTA. Disaggregated spheroids were then washed in HBSS and then plated into 96 well plates ($1\times10^3$ cells per well) and incubated at 37° C. for four days. Chemosensitivity was assessed using the NM assay as described elsewhere (Phillips et al, 1992).

The role of NQ01 in the activation of E09 at pHe values of 7.4 and 6.0 was evaluated using the NQO1 inhibitor Flavone Acetic Acid (FAA), details of which are described elsewhere (Phillips, 1999). FAA is a competetive inhibitor of NQO1 with respect to NADH and at a final concentration of 2 mM, inhibition of NQO1 is >95% whereas the activity of cytochrome P450 reductase and cytochrome b5 reductase is not substantially altered (<5% inhibition). Briefly, H460 cells (NQO1 rich) were plated into 96 well plates at a density of $2\times10^3$ cells per well. Following an overnight incubation at 37° C., medium was replaced with fresh medium (pH 7.4) containing a non-toxic concentration of FAA (2 mM) and incubated for one hour at 37° C. Medium was then replaced with fresh medium containing E09 (range of drug concentrations) and FAA (2 mM) at either pHe 7.4 or 6.0. Following a further one hour incubation at 37° C., cells were washed twice with HBSS and incubated at 37° C. in growth medium for five days. Chemosensitivity was determined by the NM assay as described above and results were expressed in terms of $IC5_0$ values, selectivity ratios ($IC_{5o}$ at pHe 7.4/IC50 at pHe 6.0) and protection ratios (ICSO FAA/E09 combinations/IC50 for E09 alone).

Substrate specificity. The influence of acidic pHe on substrate specificity for purified human NQ01 was determined as described previously (Phillips 1996, Walton et al, 1991). NQ01 mediated reduction of the quinone to the hydroquinone species is difficult to detect by conventional assays thereby necessitating the use of a reporter signal generating step. In this assay, the hydroquinone acts as an intermediate electron acceptor which subsequently reduces cytochrome c which can readily be detected spectrophotometrically. Recombinant human NQ01 was derived from E. coli transformed with the pKK233-2 expression plasmid containing the full length cDNA sequence for human NQ01 isolated from the (Beall et al, 1994). Following IPTG induction, NQO1 was purified by cybacron blue affinity chromatography, details of which are described elsewhere (Phillips, 1996). The purified protein had a molecular weight of approximately 31 kDa and a specific activity of 139/Amol DCPIP reduced/min/mg protein (Phillips, 1996). Reduction of E09 by recombinant human NQO1 was determined at pH 6.0 and 7.4 by measuring the rate of reduction of cytochrome c was measured at 550 nm on a Beckman DU 650 spectrophotometer according to previously published methods (Phillips, 1996). Results were expressed in terms of, umol cytochrome c reduced/min/mg protein using a molar extinction coefficient of 21.1 $mM^{-1}$ $cm^{-1}$ for cytochrome c.

Measurement of intracellular pH. Intracellular pH was determined using the fluorescent pH indicator BCECF (2,7-bis-(2-carboxy-ethyl)-5-(and -6) carboxyfluorescein (Molecular Probes, Eugene, USA) according to manufacturers instructions. Confluent flasks of cells were washed with HBSS to remove any traces of serum containing RPMI medium and then incubated with the esterified form of BCECF (BCECF-AM) at a concentration of 2 [tM in HBSS for one hour at 37° C. The non-denaturing detergent Pluronic was added to the probe to aid dispersion. Cells were then washed to remove all traces of BCECF-AM and then trypsinized before being suspended in serum-free/phenol red-free RPM1 medium (Gibco BRL, Paisley, UK) at a concentration of $10^6$ cells per ml at pH 6 for one hour. Flourescence measurement was determined in a Perkin-Elmer fluorescence spectrophotometer in UV grade disposable 4 ml cuvettes (Fischer Scientific) with excitation wavelengths 500 nm and 450 nm (excitation bandpass slit of 10 nm) and emission wavelength fixed at 530 nm (emission bandpass slit of 2.5 nm). These were determined to be optimal settings for the machine and system under study. An in-situ calibration was performed for every pHi determination with a range of six pH's from 4 to 9 using the ionophore nigericin at a concentration of 22.8 p, M to equilibrate pHe with pHi. Calculation of the ratio of fluorescence at 500 nm/450 nm was calculated after subtraction of background fluorescence from blanks at each pH (serum free, phenol red free RPMI without cells).

Activity of NQO1 in tumor and normal bladder specimens. The biochemical activity of NQO1 in paired samples of tumor (grade/stage ranging from G2 pTa to G2/G3 T4) and normal bladder mucosa (with three cystectomy specimens) taken from a series of 20 patients is presented in table 1. Within the tumor specimens, a broad range of NQO1 activity existed ranging from 571.4 nmoUmin/mg to undetectable (<0.1 nmol/min/mg). In histologically normal bladder mucosa specimens, NQO1 activity ranged from 190.9 to <0.1 nmoUmin/mg. In the majority of patients NQO1 activity in the tumor was greater than in the normal bladder mucosa. Tumor grade and stage did not correlate with NQO1 activity (table 1).

Validation of NQO1 antibody and immunohistochemical localization of NQ01. Western blot analysis demonstrates that polyclonal anti rat NQO1 antibody cross reacts with human NQO1 with a single band at approximately 31 kDa observed for both cell extracts and purified human NQO1. Titration of purified NQO 1 results in a decrease in band intensity and in cell extracts, band intensity was qualitatively consistent with NQO1 enzyme activity. In addition, the antibody does not detect NQO1 in the BE cell line which is devoid of NQ01 activity as a result of the C609T polymorphism. No non-specific bands were observed on Western blots. Superficial and invasive tumors with high to intermediate levels of NQO1 as determined by biochemical assays (patient numbers 1, 4 and 5 in table 1) clearly stained positive for NQO1. Staining was confined to the cytoplasm of tumor cells with little or no staining of stromal cells.

In other tumors with intermediate or low levels of NQOI activity, staining was heterogeneous with pockets of cells containing high levels of NQ01 protein. Normal bladder wall sections were obtained from a patient who underwent cystectomy (G3pT4 bladder tumor), ureter and urethra were obtained from another patient who underwent cystectomy (G3 pT3a bladder tumor). In the bladder wall, no NQO1 staining was observed in the urothelium although slight staining was present in smooth muscle layers. The urethra was negative although cells on the luminal surface of the ureter were positively stained. The basal layers of the ureter lining were however negatively stained. No evidence of invasive malignancy or in situ carcinoma were observed in the ureter and urethra or in the section of bladder wall presented. In 16 other normal bladder biopsy and cystectomy specimens, no positive staining of the urothelium was observed.

Influence of pH on substrate specificity and chemosensitivity. The ability of E09 to serve as a substrate for NQO1 was not influenced by pH with specific activities of 21.10±2.3 and 21.30±1.5 pmol cytochrome c reduced/min/mg protein at pH 7.4 and 6.0 respectively. The response of a panel of cell lines with a range of NQO1 activity (<1.0 to 1,898±276 nmol/min/mg) to E09 and MMC at pHe values of 7.4 and 6.0 is presented in table 2. At pHe=7.4, a good correlation existed between NQO1 activity and chemosensitivity to E09. In the case of MMC (table 2), a relationship between NQ01 and chemosensitivity was apparent (at pHe 7.4) although this relationship was not as prominent as shown by E09 with a narrow range of $_{IC50}$ values (range 0.9 to 7.0 ttM) observed in cell lines which cover a broad range of NQ01 activity (ranging from <1.0 to 1,898 nmol/min/mg). Both MMC and E09 are preferentially more toxic to cells at pHe values of 6.0 although much greater potentiation of E09 activity is seen with SR values (SR=selectivity ratio defined as $IC_{50}$ pHe 7.4/$_{IC50}$ pHe 6.0) ranging from 3.92 to 17.21 for E09 compared with 1.02 to 4.50 for MMC (table 2). The activity of E09 was enhanced in both NQO1 rich and deficient cell lines when pHe was reduced to 6.0 and the relationship between NQO1 and chemosensitivity remained good when cells were exposed to E09 under acidic conditions. No cell kill was observed in control cultures when the pHe was decreased to 6.0 (in the absence of drug) as determined by the MTT assay. The response of H460 cells to E09 at pHe values of 7.4 and 6.0 in the presence and absence of FAA (2 mM) is presented in table 3. At both pHe values, the response of H460 cells to E09 was reduced in the presence of FAA. Protection ratios defined as the 1050 for E09 plus FAA divided by the 1050 value for E09 alone were similar for cells under acidic and physiological pHe values (14.63 and 13.95 respectively, table 3). Selectivity ratios defined as the 1050 at pHe 7.4 divided by the 1050 at pHe 6.0 in the presence and absence of FAA were also similar with SR values of 6.31 and 6.02 for E09 alone and E09 plus FAA respectively (table 3). The response of HT-29 multicell spheroids to E09 demonstrate that spheroids exposed to E09 at pHe 6.0 were significantly more responsive than at pHe 7.4 with IC50 values of 9.89±0.89 and 24.24±3.29 AM respectively. Spheroids were significantly less responsive to E09 than the same cells exposed to E09 as monolayers at both pHe values with ratios of 1050 values for spheroids to monolayers of 202 and 341 at pHe values of 7.4 and 6.0 respectively.

Influence of acidic pHe conditions on pHi. PM values following a one hour incubation at pHe 6.0 were 6.44±0.04, 6.51±0.02 and 6.42±0.05 in A549, RT112/83 and A2780 cells respectively. Addition of the ionophore nigericin (after a one hour incubation at pHe 6.0) resulted in the equilibration of pHe and p11i.

In terms of bioreductive drug development, two of the critical factors which will ultimately determine selectivity are the enzymology of tumors and the presence of hypoxia (Workman, 1994). As outlined in the introduction, the presence or absence of NQ01 is central to the design of appropriate E09 based therapeutic strategies aimed at targeting either the aerobic (NQO1 rich cells) or hypoxic fraction (NQO1 deficient tumors) of tumors. Workman (1994) has outlined a proposed mechanism for the different properties of E09 under aerobic and hypoxic conditions based on the hypothesis that it is the semiquinone (product of one electron reduction) rather than the hydroquinone which is responsible for toxicity. In NQO1 deficient cells, the semiquinone produced as a result of one electron reductases would be relatively non-toxic as it would rapidly redox cycle back to the parent compound. Free radical species generated as a result of redox cycling would be detoxified by superoxide dismutase or catalase but under hypoxic conditions, the semiquinone would be relatively stable. If this were the major toxic species, then the activity of E09 against cells with low NQO1 would be potentiated. In NQO1 rich cells however, the major product formed would be the hydroquinone. Aerobic toxicity could be generated as a result of the back oxidation of the hydroquinone to the semiquinone species or the parent quinone (Butler et al, 1996) resulting is free radical generation. Under hypoxic conditions however the hydroquinone will be more stable and if this is relatively nontoxic, then the activity of E09 against NQO1 cells under hypoxia would not be potentiated. Whilst the mechanism of action of E09 under aerobic and hypoxic conditions is complex, the biological data suggest that E09 should target the aerobic fraction of NQO1 rich tumors or the hypoxic fraction of NQO1 deficient tumors (Workman, 1994).

Analysis of NQ01 activity in tumor and normal bladder tissues has clearly identified patients whose tumors are either NQO1 rich or NQO1 deficient (table 1). Within the subset of NQ01 rich tumors, enzyme activity is elevated relative to the normal bladder urothelium. Immunohistochemical studies confirm these biochemical measurements with staining confined to tumor cells as opposed to normal stromal cells. Within normal bladder tissues, NQ01 staining was absent from the urothelial lining of the bladder and the urethra. Faint staining of the superficial layers of the ureter was observed although the underlying basal layers of the ureter were negatively stained. Similarly, faint staining of the smooth muscle layers of the bladder, ureter and urethra were also observed. These studies suggest that a proportion of patients with bladder tumors (at various grades and stages of the disease)

exhibit a significant differential in terms of NQO1 activity which could potentially be exploited by E09 based therapies directed against the aerobic fraction of tumor cells. With regards to the ability of E09 to selectively kill hypoxic NQO1 deficient cells, a subset of patients also exist whose tumors are devoid of NQ01 activity (table 1). It is not known whether or not bladder tumors contain regions of low oxygen tension and further studies are required using hypoxia markers such as pimonidazole (Kennedy et al, 1997) to address this issue and to establish the relationship between NQ01 activity and hypoxia in tumors.

Whilst biochemical and immunohistochemical studies demonstrate that a subset of patients exist which have the appropriate tumor enzymology to activate E09 (under aerobic conditions), intravesical chemotherapy can result in systemic toxicity due to the drug entering the blood supply. This study has also evaluated a potential strategy for minimizing any risk of systemic toxicity based upon the hypothesis that administration of E09 in an acidic vehicle would enhance the potency of E09 (Phillips et al, 1992) within the bladder and that any drug reaching the blood stream would become relatively inactive due to a rise in pHe. Selectivity for aerobic cells would still be determined by NQO1 activity and therefore it is essential to determine the role that NQO1 plays in the activation of E09 under acidic pHe conditions. In a panel of cell lines with a broad spectrum of NQO1 activity, reducing the pHe to 6.0 enhances the potency of E09 under aerobic conditions in all cases (with SR values ranging from 3.92 to 17.21, table 2). In the case of MMC, potency is also enhanced at low pHe values although the magnitude of the pH dependent increase in toxicity is reduced (SR values ranging from 1.02 to 4.50, table 2) compared with E09. With respect to MMC, one explanation for increased activity under acidic conditions has been attributed to the fact that MMC becomes a substrate for NQO1 under acidic conditions (Pan et al, 1993, Siegel et al, 1993). This is not the case with E09 as rates of reduction of E09 by purified human NQO1 are not influenced by pH ($21.10 \pm 2.30$ and $21.30 \pm 1.50$ limol cytochrome c reduced/min/mg protein at pH 7.4 and 6.0 respectively). Recent studies have demonstrated that the activity of E09 is enhanced under acidic conditions (pHe=6.5) but only when the intracellular pH is reduced (plli=6.5) by co-incubation with nigericin (Kuin et al, 1999). The results of this study are in agreement with this finding as pHi becomes acidic (pHi values range from $6.42 \pm 0.05$ to $6.51 \pm 0.02$ depending on the cell line) when cells are cultured under pHe 6.0 conditions.

In the panel of cell lines used in this study, a good correlation exists between NQO1 activity and chemosensitivity at both pHe values of 7.4 and 6.0. A strong relationship between NQO1 activity and response under aerobic conditions (at pHe 7.4) has been established previously by several groups (Robertson et al, 1994, Fitzsimmons et al, 1996, Smitkamp-Wilms et al, 1994) and there is clear evidence that NQ01 plays a central role in the mechanism of action of E09 under aerobic conditions (Workman, 1994). The good correlation between NQ01 activity and response at pHe 6.0, in conjunction with the fact that E09 is still a good substrate for NQO1 at pH 6.0, suggests that NQO1 plays a significant role in E09's mechanism of action at acidic pHe values under aerobic conditions. It is of interest to note however that the activity of E09 against BE cells (which are devoid of NQ01 activity as a result of the C609T polymorphism, Traver et al, 1992) is also enhanced under acidic pHe conditions (table 2). This suggests that there is a NQO1 independent mechanism for the increased activity of E09 under acidic conditions. This is confirmed by the use of the NQ01 inhibitor FAA where the 'protection ratios' (defined as the ratio of $IC_{50}$ values for E09 plus FAA divided by the ICSo values for E09) are similar at both pHe 7.4 and 6.0 (13.95 and 14.63 respectively, table 3). If NQO1 played a central role in the activation of E09 at pHe 6.0, then the protection ratio at pHe 6.0 would be significantly greater than the protection ratio at pHe 7.4. The mechanism behind the NQ01 independent activation of E09 is unclear although it is a well known fact that the reactivity of aziridine ring structures is enhanced by protonation resulting in ring opening to the aziridinium ion which is a potent alkylating species (Mossoba et al, 1985, Gutierrez, 1989). Alternatively, E09 is a substrate for other one electron reductases (Maliepaard et al, 1995, Saunders et al, 2000) and further studies designed to evaluate whether E09's metabolism by these enzymes is pH dependent needs to be determined. The potency of E09 can be enhanced further by reducing pHe below 6.0 (Phillips et al, 1992) but these conditions are unlikely to provide significant clinical benefits as E09 becomes progressively more unstable when pH is reduced to 5.5 (t'/s=37 min). From a pharmacological standpoint, administration of E09 in a vehicle at pH 6.0 would appear desirable. Not only would this result in significant enhancement of E09 activity but also the stability of E09 would be sufficient (tlh=2.5 h) to maintain drug exposure parameters at a therapeutic level.

With regards to the activity of E09 against three dimensional culture models in vitro, this study has demonstrated that reducing the pHe to 6.0 enhances the potency of E09 against multicell spheroids although the magnitude of this effect is reduced compared with monolayer cultures. It is not known whether or not reduction in pHe results in greater cell kill throughout the spheroid or if it is confined to the surface of the spheroid exposed to medium. In comparison with MMC, previous studies using histocultures exposed to MMC demonstrated that no difference in toxicity exists between physiological and acidic pHe conditions (Yen et al, 1996). The pH dependent increase in E09 toxicity against spheroids suggests that manipulation of pHe may not only be of use in treating a multilayered solid bladder tumor but may offer an advantage over MMC. It should however be stated that multicell spheroids are significantly less responsive to E09 than mono] ayers, presumably because of the poor penetration properties of E09 through avascular tissue (Phillips et al, 1998). E09 can nevertheless kill >90% of cells in spheroids suggesting that a higher doses at least, the penetration of E09 is sufficient to eradicate cells which reside some distance away from the surface of the spheroid.

In conclusion, the results of this study have demonstrated that within a population of patients with bladder tumors at various stages and grades of the disease, there exists a great heterogeneity regarding the expression of NQO1. The majority of patients have tumors possessing elevated levels of NQO 1 while a small subset of patients appear to be devoid of NQO1 activity. The heterogeneous nature of NQO1 activity described here is consistent with several other studies in various tumor types (Malkinson et al, 1992, Smitkamp-Wilms et al, 1995, Siegel et al, 1998). These findings reinforce the view that 'enzyme profiling' of individual patients could be valuable prior to therapeutic intervention with bioreductive drugs (Workman, 1994). This is to our knowledge the first study to characterize NQO1 activity and cellular localization in bladder tumors and provide strong evidence to support the evaluation of E09 against superficial and locally invasive bladder tumors. This study has clearly demonstrated that under aerobic conditions, E09 is much more potent under acid conditions (pH6.0) than at physiological pH (pH7.4). The mechanism for this increased E09 potency appears to be NQ01 independent and whilst this will not improve (or reduce) selectivity, it may prove beneficial in terms of reducing the therapeutically effective dose of E09. Dose reduction in conjunction with the fact that a reduction in the potency of E09 due to the increased pHe in the blood stream suggests that systemic toxicity arising from the intravesical administration of E09 would be low. In addition, this study shows that under physiological conditions the activity of E09 is much lower in tissues with "normal" expression of NQO1 compared to "high" NQO1 expressing tissues (i.e. the tumors). The results of this study provide strong evidence in support of the proposal that intravesical administration of E09 may have activity against bladder tumors.

REFERENCES

Butler J, Spanswick V J and Cummings J (1996) The autooxidation of reduced forms of E09. *Free Rad Res* 25: 141-148.

Bradford M M (1976) A rapid and sensitive method for the quantification of microgram quantities of protein utilising the principle of protein-dye binding. *Anal Biochem* 72: 248-254.

Connors T A (1996) Bioreductive agents, hypoxic cells and therapy. *Eur J Cancer* 32A: 1833-1834.

Cummings J, Spanswick V J, Tomaz M and Smyth J F (1998a) Enzymology of MMC metabolic activation in tumor tissue. Implications for enzyme directed bioreductive drug development. *Biochem Pharmacol* 56: 405-414.

Cummings J, Spanswick V J, Gardiner J, Ritchie A and Smyth, I F (1998b) Pharmacological and biochemical determinants of the antitumour activity of the indoloquinone E09. *Biochem Pharmacol* 55: 253-260.

Dirix L Y, Tonnesen F, Cassidy J, Epelbaum R, Huinink W W T, Pavlidis N, Sorio R, Gamucci T, Wolff I, Tevelde A, Lan J, and Verweij J (1996) E09 phase II study in advanced breast, gastric, pancreatic and colorectal carcinoma by the early clinical studies group. *Eur J Cancer* 32A: 2019-2022.

Fitzsimmons S A, Workman P, Greyer M, Paull K, Camalier R and Lewis A D (1996) Reductase enzyme expression across the National Cancer Institute tumor cell line panel: Correlation with sensitivity to MMC and E09. *J Natl Cancer Inst* 88: 259-269 Gutierrez P L (1989) Mechanism of bioreductive alkylation. The example of diazaquinone (AZQ. *Free Radical Bio Med* 6: 405-445.

Hendriks H R, Piazo P E, Berger D P, Kooistra K L, Bibby M C, Boven E, Dreef-Van Der Meulen H C, Henrar-R E C, Fiebig H H, Double J A, Hornstra H W, Pinedo H M, Workman P and Swartsmann G (1993) E09: A novel bioreductive alkylating indoloquinone with preferential solid tumor activity and lack of bone marrow toxicity in preclinical models. *Eur J Cancer* 29A: 897-906.

Herr H W (1987) Intravesical therapy—a critical review. *Urology Clinics of N America* 14: 399-404.

Hodnick W F and Sartorelli A C (1997) Measurement of dicumarol sensitive NADPH: (menadione cytochrome c) oxidoreductase activity results in an artifactual assay of DT-diaphorase in cell sonicates. *Anal Biochem* 252: 165-168.

Kennedy A S, Raleigh J A, Perez G M, Calkins D P, Thrall D E, Novotny D B, Varia M A (1997) Proliferation and hypoxia in human squamous cell carcinoma of the cervix: first report of combined immunohistochemical assays. *Int J Radiat Oncol Biol Phys* 37: 897-905.

Kuin A, Alders M, Lamfers M, Van Zuidam D J, Essers M, Beijnen J H and Smets L A (1999) Potentiation of anti-cancer activity at low intratumoural pH induced by the mitochondrial inhibitor m-iodobenzylguanidine (MIBG) and its analogue benzylguanidine (BG). *Br J Cancer* 79: 793-801.

Maffezzini M, Simonata A, Zanon M, Raber M and Carmigani G (1996) Up-front chemotherapy for low stage low grade recurrent bladder cancer. *J Urol* 155: 91-93.

Malkinson A M, Siegel D, Forrest G L, Gazdar A F, Oie H K, Chan D C, Bunn P A, Mabry M, Dykes D J, Harrison S D and Ross D (1992) Elevated NQO1 activity and messenger RNA content in human non small cell lung carcinoma—Relationship to the response of lung tumor xenografts to MMC. *Cancer Res* 52: 4752-4757.

Maliepaard M, Wolf A, Groot S E, De Mol N J and Janssen L H M (1995) Indoloquinone E09: DNA interstrand cross linking upon reduction by DT-diaphorase or xanthine oxidase. *Br J Cancer* 71: 836-839.

Mossoba M M, Alizadeh M and Gutierrez P L (1985) Mechanism for the reductive activation of diazaquinone. *J Pharm Sci* 74: 1249-1254.

Newling D (1990) Intravesical therapy in the management of superficial transitional cell carcinoma of the bladder: the experience of the EORTC GU group. *Br J Cancer* 61: 497-499.

Oosterlink W, Kurth K H, Schröder F, Bultinck J, Hammond B, Sylvester R, and members of the European Organisation for Research and Treatment of Cancer Genitourinary Group (1993) A prospective European Organisation for Research and Treatment of Cancer Genitourinary Group randomised trial comparing transurethral resection followed by a single instillation of epirubicin or water in single stage Ta, T 1 papillary carcinoma of the bladder. *J Urol* 149: 749-752.

Pan S S, Yu F and Hipsher C (1993) Enzymatic and pH modulation of MMC induced DNA damage in MMC resistant HCT 116 human colon cancer cells. *Mol Pharmacol* 43: 870-877.

Phillips R M, Hulbert P B, Bibby M C, Sleigh N R, and Double J A (1992) In vitro activity of the novel indoloquinone EO-9 and the influence of pH on cytotoxicity. *Br J Cancer* 65: 359-364.

Phillips R M (1996) Bioreductive activation of a series of analogues of 5-aziridinyl-3hydroxymethyl-1-methyl-2-[1H-indolo-4,7-dione]prop-(3-en-a-ol (E09) by human NQO1. *Biochem Pharmacol* 52: 1711-1718.

Phillips R M, Loadman P M and Cronin B P (1998) Evaluation of a novel in vitro assay for assessing drug penetration into avascular regions of tumors. *Br J Cancer* 77: 2112-2119.

Phillips R M (1999) Inhibition of DT-diaphorase (NAD(P) H:quinone oxidoreductase, EC 1.6.99.2) by 5,6-dimethylxanthenone-4-acetic acid (DNIXAA) and flavone-8acetic acid (FAA): Implications for bioreductive drug development. *Biochem Pharmacol* 58: 303-310.

Plumb J A and Workman P (1994) Unusually marked hypoxic sensitisation to indoloquinone E09 and MMC in a human colon tumor cell line that lacks NQOI activity. *Int J Cancer* 56: 134-139.

Robertson N, Haigh A, Adams G E and Stratford U (1994) Factors affecting sensitivity to E09 in rodent and human tumor cells in vitro: NQ01 activity and hypoxia. *Eur J Cancer* 30A: 1013-1019.

Saunders M P, Jaffar M, Patterson A V, Nolan J, Naylor M A, Phillips R M, Harris A L and Stratford H (2000) The relative importance of NADPH:cytochrome c (P450) reductase for determining the sensitivity of human tumor cells to the indoloquinone E09 and related analogues lacking functionality at the C-2 and C-3 positions. *Biochem Pharmacol* 59: 993-996.

Schellens J H M, Planting A S T, Van Acker B A C, Loos W J, De Boer-Dennert M, Van Der Burg M E L, Koier I, Krediet R T, Stoter G and Verweij J (1994) Phase I and pharmacologic study of the novel indoloquinone bioreductive alkylating cytotoxic drug E09. *J Natl Cancer Inst* 86: 906-912.

Schlager J J and Powis G (1988) MMC is not metabolised by but is an inhibitor of human kidney NAD(P)H:(quinone acceptor) oxidoreductase. *Cancer Chemother Pharmacol* 22: 126-130.

Siegel D, Gibson N W, Preusch P C and Ross D (1990) Metabolism of MMC by NQ01: Role in MMC induced DNA damage and cytotoxicity in human colon carcinoma cells. *Cancer Res* 50: 7483-7489.

Siegel D, Beall H D, Kasai M, Gibson N W and Ross D (1993) PH dependent inactivation of NQ01 by MMC and porfiromycin. *Mol Pharmacol* 44: 1128-1134. Siegel D, Franklin W A and Ross D (1998) Immunohistochemical detection of NAD(P)H:Quinone oxidoreductase in human lung and lung tumors. *Clin Cancer Res* 4: 2065-2070.

Smitkamp-Wilms E, Peters G J, Pinedo H M, Van Arkotte J and Giaccone G (1994) Chemosensitivity to the indoloquinone E09 is correlated with NQ01 activity and gene expression. *Biochem Pharmacol* 47: 1325-1332.

Smitskamp-Wilms E, Giaccone G, Pinedo H M, Van Der Laan B F A M and Peters G J (1995) NQ01 activity in normal and neoplastic human tissues: An indicator of sensitivity to bioreductive agents?. *Br J Cancer* 72: 917-921.

Tolley D A, Parmar M K B, Grigor K M, Lallemand G and the Medical Research Council superficial bladder cancer working party (1996) The effect of intravesical MMC on recurrence of newly diagnosed superficial bladder cancer: A further report with 7 years of followup. J Urol 155: 1233-1238.

Traver R D, Horikoshi T, Dannenberg K D, Stadlbauer T H W, Dannenberg P V, Ross D and Gibson N W (1992) NAD (P)H:quinone oxidoreductase gene expression in human colon carcinoma cells: Characterisation of a mutation which modulates NQ01 activity and mitomycin sensitivity. *Cancer Res* 52: 797-802.

Walton M I, Smith P J and Workman P (1991) The role of NAD(P)H:quinone reductase (EC 1.6.99.2, NQ01) in the reductive bioactivation of the novel indoloquinone antitumour agent E09. *Cancer Commun* 3: 199-206.

Workman P (1994) Enzyme directed bioreductive drug development revisited: A commentary on recent progress and future prospects with emphasis on quinone anticancer drugs and quinone metabolising enzymes, particularly NQ01. *Oncol Res* 6: 461-475.

Yen W C, Schmittgen T and Au J L (1996) Different pH dependency of mitomycin C activity in monolayer and three dimensional cultures. *Pharmaceut Res* 13: 1887-1891.

TABLE 1

Tumor histology reports and NQO1 activity in paired samples of bladder tumor and normal bladder mucosa.

| Patient No. | Tumor histology | NQO1 Activity Tumor (nmol/min/mg) | NQO1 Activity Normal (nmol/min/mg) | Ratio of NQO1 levels in tumor to normal tissue. |
|---|---|---|---|---|
| 1[f,s,i,p] | G2 pTa | 571.4 | <0.1 | 571. |
| 2[m,s,r] | G3 pT2 | 273.3 | <0.1 | 273. |
| 3[f,s,i] | G1pTa | 107.80 | <0.1 | 107. |
| 4[m,e,i] | G3 pT2/3 | 73.36 | <0.1 | 73.3 |
| 5[m,s,i] | G3pT4 (0' | 81.30 | 4.10 | 19.8 |
| 6[h] | G2PT1 | 309.50 | 25.20 | 12.1 |
| 7[m,n,r,o] | G3 pT2 | 10.00 | <0.1 | 10.0 |
| 8[f,n,i] | G3pT2 | 9.80 | <0.1 | 9.80 |
| 9[m,n,i] | G2 pT2 | 4.40 | <0.1 | 4.40 |
| 10[m,s,c] | G3 pT2 | 34.01 | 8.50 | 4.00 |
| 11[m,s] | G 1 pTa | 69.76 | 22.20 | 3.14 |
| 12,,n | G1pTa | 42.16 | 15.30 | 2.73 |
| 13[m,n,i] | G3 pT2 | 179.6 | 72.12 | 2.49 |
| 14[m,e,i] | G2/G3 T4 (C) | 89.70 | 63.30 | 1.41 |
| 15[m,n,r] | G3 pT2 | 0.40 | <0.1 | 0.40 |
| 16[m,e,c,o] | G3 PT3 (C) | 21.60 | 61.70 | 0.35 |
| 17[f,n,i] | G2 PTI | 58.40 | 190.90 | 0.30 |
| 18[m,e,o] | G2 PTI | <0.1 | <0.1 | 0 |
| 19[f,n,i] | G2 PT I. | <0.1 | <0.1 | 0 |
| 20[m,e,c,r] | G2 pT0 | <0.1 | <0.1 | 0 |

[m]Male,
[f]Female,
[s]Smoker,
[n]Non-smoker,
[e]Ex-smoker,
[o]Intravesical chemotherapy prior to specimen collection,
[r]Radiotherapy prior to specimen collection,
[i]First presentation,
P Previous malignancy other than bladder,
[h]No medical history available,
[o]Possible occupational carcinogen exposure (i.e., dye industry worker).
(C) denotes cystectomy specimens. In all cases, protein levels following preparation of the cytosolic fraction were greater than 0.1 mg/ml.

TABLE 2

The relationship between NQ01 activity and chemosensitivity to E09 and MMC under physiological and acidic pHe conditions.

| Cell line | Drug | NQO1 (nmol/min/mg) | IC50 pHe 7.4 (nM) | IC50 pHe 6.0 (nM) | SR* |
|---|---|---|---|---|---|
| H460 | E09 | 1652 ± 142 | 60 ± 10 | 9.5 ± 2 | 6.31 |
| HT-29 | E09 | — 688 ± 52 | 120 ± 53 | 29 ± 10 | 4.13 |
| T24/83 | E09 | 285 ± 28 | 290 ± 65 | 60 ± 18 | 4.83 |
| A2780 | E09 | 159 ± 33 | 200 ± 50 | 51 ± 14 | 3.92 |
| EJ138 | E09 | 83 ± 14 | 310 ± 95 | 39 ± 7 | 7.94 |
| RT112 | E09 | 30 ± 3 | 1050 ± 75 | 61 ± 13 | 17.21 |
| BE | E09 | <0.1 | 5300 ± 169 | 1300 ± 75– | 4.07 |
| H460 | MMC | 1652 ± 142 | 900 ± 200 | 220 ± 130 | 4.50 |
| HT-29 | MMC | 688 ± 52 | 1050 ± 210 | 500 ± 240 | 2.10 |
| T24/83 | MMC | 285 ± 28 | 2150 ± 93 | 2100 ± 800 | 1.02 |
| A2780 | MMC | 159 ± 33 | 2400 ± 340 | 1400 ± 130 | 1.71 |
| EJ138 | MMC | 83 ± 14 | 1600 ± 200 | 1400 ± 250 | 1.14 |
| RT112 | MMC | 30 ± 3 | 3350 ± 250 | 2000 ± 500 | 1.67 |
| BE | MMC | <0.1 | 7000 ± 192 | 4400 ± 215 | 1.59 |

All results presented are the mean of 3 independent experiments (SD values omitted in the interests of presentation).
*SR (selectivity ratio) = IC5o at pH 7.4/IC5o at pH 6.0

TABLE 3

Response of H460 cells to E09 in the presence or absence of FAA (2 mm) at pHe values of 7.4 and 6.0.

| Drug | pHe | IC5o (nM) | SR* | PR** |
|---|---|---|---|---|
| E09 | 7.4 | 60.0 ± 8.1 | ' | — |
| E09 | 6.0 | 9.5 ± 2.6 | 6.31 | — |
| E09/FAA | 7.4 | 837 ± 45 | — | 13.95 |
| E09/FAA | 6.0- | 139 ± 27 | 6.02 | 14.63 |

*SR = Selectivity Ratio defined as the ratio of IC5o values at pHe = 7.4 divided by the $IC_{50}$ at pHe = 6.0.
**Plf = Protection ratio defined as the ratio of $IC_{50}$ values for E09 plus FAA divided by the IC5o values for E09 alone.
All values represent the mean ± standard deviation for three independent experiments.

TABLE 4

| | | Neoquin 8 mg/vial lyophilised product | | | | |
| --- | --- | --- | --- | --- | --- | --- |
| | | time (months) | | | | |
| Storage | test item | 0 | 1 | 2 | 3 | 6 |
| 5° C. | content* | 102.7 ± 1.2 | na | na | 103.8 ± 0.8 | 100.6 ± 0.6 |
| | purity** | 99.9 ± 0.008 | na | na | 99.5 ± 0.03 | 99.6 ± 0.03 |
| | residual moisture*** | 6.0% | na | na | 7.0% | 6.3% |
| | pH after reconstitution**** | 9.5 | na | na | na | 9.4 |
| 25° C./60% RH | content | 102.7 ± 1.2 | 103.4 ± 0.7 | 102.1 ± 0.2 | 102.6 ± 1.3 | 97.4 ± 1.0 |
| | purity | 99.9 ± 0.008 | 99.9 ± 0.05 | 99.9 ± 0.01 | 99.2 ± 0.07 | 98.7 ± 0.2 |
| | residual moisture | 6.0% | na | na | 5.9% | 5.9% |
| | pH after reconstitution**** | 9.5 | na | na | na | 9.4 |
| 40° C./75% RH | content | 102.7 ± 1.2 | 102.3 ± 1.1 | 100.4 ± 1.3 | 101.3 ± 0.2 | 86.4 ± 2.0 |
| | purity | 99.9 ± 0.008 | 99.8 ± 0.01 | 99.7 ± 0.04 | 98.4 ± 0.07 | 97.5 ± 0.2 |
| | residual moisture | 6.0% | na | na | 6.2% | 6.3% |
| | pH after reconstitution**** | 9.5 | na | na | na | 9.5 |

*content as % of labelled content n = 3
**purity as chromatographic purity n = 3

What is claimed is:

1. A drug delivery system comprising:
   a composition comprising EO9 and propylene glycol; and
   a catheter.

2. The drug delivery system of claim 1, further comprising sodium bicarbonate.

3. The drug delivery system of claim 1, further comprising disodium edetate.

4. The drug delivery system of claim 1, comprising about 0.5 mg to about 16 mg of EO9.

5. The drug delivery system of claim 1, further comprising water and propylene glycol at a 40:60 V/V ratio of water to propylene glycol, in combination with 2% sodium bicarbonate and 0.02% disodium edetate.

* * * * *